United States Patent
Gajewski et al.

(12) 
(10) Patent No.: US 6,559,170 B1
(45) Date of Patent: May 6, 2003

(54) PYRIDINE DERIVATIVES HAVING FUNGICIDAL ACTIVITY AND PROCESSES TO PRODUCE AND USE SAME

(75) Inventors: Robert Peter Gajewski, Indianapolis, IN (US); Neil Vincent Kirby, Carmel, IN (US); Brent Jeffrey Rieder, Greenfield, IN (US); Chrislyn Marie Carson, Carmel, IN (US); Zhengyu Huang, Carmel, IN (US); Stephen Lewis Wilson, Indianapolis, IN (US)

(73) Assignee: Dow AgroScience LLC, Indianapolis, IN (US)

( * ) Notice: Subject to any disclaimer, the term of this patent is extended or adjusted under 35 U.S.C. 154(b) by 0 days.

(21) Appl. No.: 10/148,105

(22) PCT Filed: Dec. 11, 2000

(86) PCT No.: PCT/US00/33623

§ 371 (c)(1),
(2), (4) Date: May 23, 2002

(87) PCT Pub. No.: WO01/44196

PCT Pub. Date: Jun. 21, 2001

Related U.S. Application Data

(60) Provisional application No. 60/170,893, filed on Dec. 15, 1999.

(51) Int. Cl.$^7$ ........................ A61K 31/44; C07D 213/62; A01M 43/40
(52) U.S. Cl. ........................ 514/348; 546/296; 546/290; 514/345
(58) Field of Search .................... 514/348, 345; 546/296, 290

(56) References Cited

U.S. PATENT DOCUMENTS

| | | | |
|---|---|---|---|
| 5,021,581 A | 6/1991 | Clough et al. | 564/309 |
| 5,089,510 A | 2/1992 | Tapolczay et al. | 514/345 |
| 5,157,037 A | 10/1992 | Schuetz et al. | 514/269 |
| 5,185,342 A | 2/1993 | Hayase et al. | 514/274 |
| 5,334,577 A | 8/1994 | Wenderoth et al. | 504/130 |
| 5,442,063 A | 8/1995 | Takase et al. | 544/333 |
| 5,466,693 A | 11/1995 | Warrington et al. | 514/269 |
| 5,585,513 A | 12/1996 | Matthews et al. | 560/60 |
| 5,770,614 A | 6/1998 | Murabayashi et al. | 514/348 |
| 5,856,573 A | 1/1999 | Takase et al. | 564/169 |
| 6,369,083 B1 * | 4/2002 | Canada et al. | 514/336 |

FOREIGN PATENT DOCUMENTS

| | | |
|---|---|---|
| EP | 0278595 A | 8/1988 |
| EP | 0307103 | 3/1989 |
| EP | 0335519 | 10/1989 |
| EP | 0373775 | 6/1990 |
| EP | 0528681 | 2/1993 |
| EP | 0781764 | 7/1997 |
| WO | WO9532182 | 11/1995 |
| WO | WO9701538 | 1/1997 |
| WO | WO9729088 | 8/1997 |
| WO | WO9823350 | 6/1998 |
| WO | WO9833772 | 8/1998 |
| WO | WO9921833 | 5/1999 |
| WO | WO9925713 | 5/1999 |

OTHER PUBLICATIONS

Takenaka, H.; Hayase, Y.; Hasegawa, R.; Ichiba, T.; Masuko, M.; Murabayashi, A.; Takeda, Reiji; Structure and Fungicidal Activities of 2–Methoxyimino–N–methyl–2–[2–(substituted pyridyloxymethyl)phenyl]acetamide Derivatives; *J. Pesticide Sci.* 23, 379–385 (1998).

Hutson, D.; Miyamoto, J.; The Strobilurin Fungicides; John Wiley & Sons; *Fungicidal Activity* (1998).

Ichinari, M.; Masuko, M.; Takenaka, H.; Hasegawa, R.; Ichiba, T.; Hayase, Y.; Takeda, R.; Structure and Fungicidal Activities of Methoxyiminophenylacetamide Derivatives; *Extended Summaries: IUPAC Congress; Pestic Sci.*; 55:343–389 (1999).

Sauter, H.; Steglich, W.; Anke, T.; Strobilurins: Evolution of a New Class of Active Substances; *Angew: Chem. Int. Ed.* 1999, 38, 1328–1349.

* cited by examiner

*Primary Examiner*—Charanjit S. Aulakh
(74) *Attorney, Agent, or Firm*—Carl D. Corvin

(57) ABSTRACT

Compounds of formula (One) wherein $A^1$, $A^2$, $A^3$, and $A^4$ independently H, halogen, or methyl; E is —N= or —CH=; G is O= or S=; J is —O—, —NH— or —NT$^1$— wherein $T^1$ is alkyl having 1 to 6 carbon atoms; $L^1$, $L^2$, and $L^3$ are independently H, halogen, cyano, methyl, monohalomethyl, dihalomethyl, or trihalomethyl; M is —S—, —S—(=O), or —S(=O)$_2$—; and Q is aryl, substituted aryl, heteroaryl, or substituted heteroaryl. The compounds are useful as fungicides.

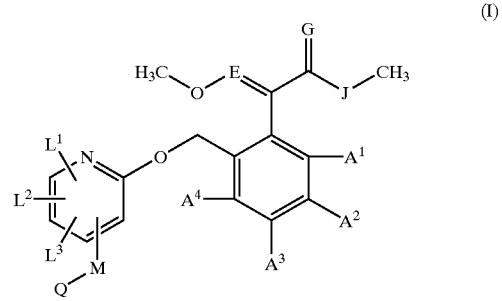

(I)

24 Claims, No Drawings

PYRIDINE DERIVATIVES HAVING FUNGICIDAL ACTIVITY AND PROCESSES TO PRODUCE AND USE SAME

CROSS-REFERENCE TO RELATED APPLICATIONS

This application claims priority from U.S. provisional application No. 60/170,893. This priority application was filed on Dec. 15, 1999.

FIELD OF THE INVENTION

This invention is related to the field of compounds having fungicidal activity and processes to produce and use same.

BACKGROUND OF THE INVENTION

Our history is riddled with outbreaks of fungal diseases that have caused widespread human suffering. One need look no further than the Irish potato famine, which occurred from 1845 to 1860, where an estimated 1,000,000 people died, and an estimated 1,500,000 emigrated, to see the effects of a fungal disease.

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop and consequently, increase the value of the crop. In most situations, the increase in value of the crop is worth at least three times the cost of the use of the fungicide. However, no one fungicide is useful in all situations. Consequently, research is being conducted to produce fungicides that are safer, that have better performance, that are easier to use, and that cost less.

In light of the above, the inventors provide this invention.

SUMMARY OF THE INVENTION

It is an object of this invention to provide compounds that have fungicidal activity.

It is an object of this invention to provide processes that produce compounds that have fungicidal activity.

It is an object of this invention to provide processes that use compounds that have fungicidal activity.

In accordance with this invention, processes to produce and processes to use compounds having a general formula according to formula one, and said compounds are provided.

While all the compounds of this invention have fungicidal activity, certain classes of compounds may be preferred for reasons such as, for example, greater efficacy, or ease of synthesis.

Throughout this document, all temperatures are given in degrees Celsius and all percentages are weight percentages, unless otherwise stated. The term "Me" refers to a methyl group. The term "Et" refers to an ethyl group. The term "Pr" refers to a propyl group. The term "ppm" refers to parts per million. The term, "psi" refers to pounds per square inch.

DETAILED DESCRIPTION OF THE INVENTION

The compounds of this invention have a formula according to formula one.

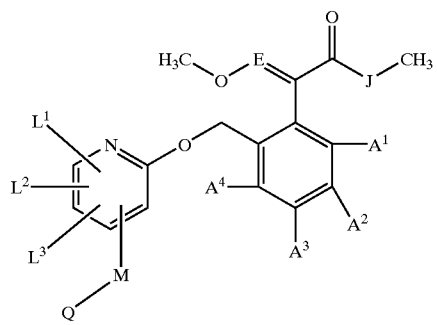

Formula One

In formula one:

$A^1$, $A^2$, $A^3$, and $A^4$ are independently selected from the group consisting of hydro (—H), halo (—F, —Cl, —Br, and —I), and methyl (—CH$_3$);

E is selected from the group consisting of aza (—N═) and methine (—CH═);

G is selected from the group consisting of oxo (O═) and thioxo (S═);

J is selected from the group consisting of oxy (—O—), amino (—NH—) and alkylamino (—NT$^1$—) where T$^1$ is an alkyl group having 1 to 6 carbon atoms;

$L^1$, $L^2$, and $L^3$ are independently selected from the group consisting of hydro (—H), halo (—F, —Cl, —Br, and —I), cyano (—CN), methyl (—CH$_3$), and mono, di, and trihalomethyl;

M is selected from the group consisting of thio (—S—), sulfinyl (—S(═O)—), and sulfonyl (—S(═O)$_2$—); and Q is selected from the group consisting of aryl (—Aryl), substituted aryl (—SAryl), heteroaryl (—HAryl), and substituted heteroaryl (—SHAryl), where "aryl" or "Ph" refers to a phenyl group and where "heteroaryl" refers to pyridyl, pyridinyl, pyrazinyl or pyridazinyl, and where said SAaryl and SHAryl have substituents that are independently selected from the group consisting $C_1$–$C_6$ alkyl, $C_1$–$C_6$ alkoxy, halo-$C_1$–$C_6$ alkyl, halo-$C_1$–$C_6$ alkoxy, halo, nitro, carbo-$C_1$–$C_6$ alkoxy, or cyano, arylalkyl, alkanoyl, benzoyl, amino, and substituted amino, preferably, hydro (—H), $C_1$–$C_6$ alkyls, arylalkyl, alkanoyl, benzoyl, amino, and substituted amino where said substituted amino has substituents that are independently selected from the group consisting of hydro (—H), alkyl, arylalkyl, alkanoyl, benzoyl, and amino.

The term "alkyl", "alkenyl", or "alkynyl" refers to a unbranched or branched chain carbon group.

The term "alkoxy" refers to a unbranched or branched chain alkoxy group.

The term "haloalkyl" refers to a unbranched or branched alkyl group substituted with one or more halo atoms. The term "haloalkoxy" refers to an alkoxy group substituted with one or more halo atoms.

In general, these compounds can be produced by reacting a compound of formula two with a compound of formula three under suitable reaction conditions.

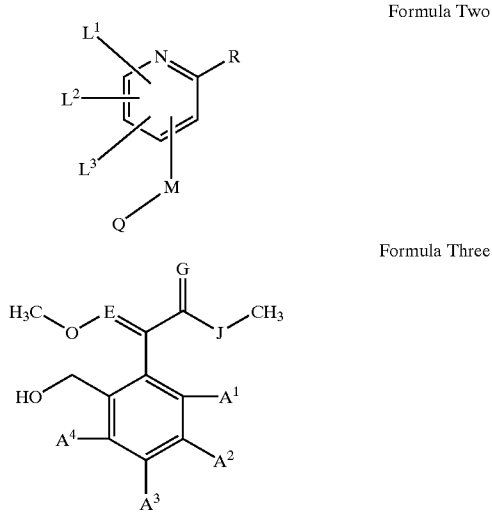

Formula Two

Formula Three

In formulas two and three, the variables are the same as in formula one and R is selected from the group consisting of halo (—F, —Cl, —Br, and —I), and alkylsulfonyl (—S(=O)$_2$—T$^2$) where T$^2$ is an alkyl group having from 1 to 6 carbon atoms.

In general, suitable reaction conditions include, the use of a strong base such as, for example, sodium hydride or potassium tert-butoxide, in a polar aprotic medium, such as, for example, tetrahydrofuran, diethylether, or dimethylsulfoxide, at temperatures that range from about 0 to about 100° C.

In general, these compounds can be used in a variety of ways. These compounds are preferably applied in the form of a formulation comprising one or more of the compounds with a phytologically-acceptable carrier. Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of one or more of the compounds.

The formulations which are applied most often are aqueous suspensions or emulsions. Such water-soluble, water suspendable, or emulsifiable formulations are either solids, usually known as wettable powders, or liquids, usually known as emulsifiable concentrates, aqueous suspensions, or suspension concentrates. The present invention contemplates all vehicles by which one or more of the compounds can be formulated for delivery and use as a fungicide.

As will be readily appreciated, any material to which these compounds can be added may be used, provided they yield the desired utility without significant interference with the activity of these compounds as antifungal agents.

Wettable powders, which may be compacted to form water dispersible granules, comprise an intimate mixture of one or more of the compounds, an inert carrier and surfactants. The concentration of the compound in the wettable powder is usually from about 10% to about 90% w/w, more preferably about 25% to about 75% w/w. In the preparation of wettable powder formulations, the compounds can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the compounds in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the compounds comprise a convenient concentration, such as from about 10% to about 50% w/w, in a suitable liquid. The compounds are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface active dispersing agents are usually employed in liquid formulations and in the amount of from 0.1 to 20 percent by weight of the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 50% w/w. Suspensions are prepared by finely grinding one or more of the compounds, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The compounds may also be applied as granular formulations, which are particularly useful for applications to the soil. Granular formulations usually contain from about 0.5% to about 10% w/w of the compounds, dispersed in an inert carrier which consists entirely or in large part of coarsely divided attapulgite, bentonite, diatomite, clay or a similar inexpensive substance. Such formulations are usually prepared by dissolving the compounds in a suitable solvent and applying it to a granular carrier which has been preformed to the appropriate particle size, in. the range of from about 0.5 to about 3 mm. Such formulations may also be prepared by making a dough or paste of the carrier and the compound, and crushing and drying to obtain the desired granular particle.

Dusts containing the compounds are prepared simply by intimately mixing one or more of the compounds in powdered form with a suitable dusty agricultural carrier, such as, for example, kaolin clay, ground volcanic rock, and the like. Dusts can suitably contain from about 1% to about 10% w/w of the compounds.

The formulations may contain adjuvant surfactants to enhance deposition, wetting and penetration of the compounds onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5%. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

The formulations may optionally include combinations which can comprise at least 1% of one or more of the compounds with another pesticidal compound. Such additional pesticidal compounds may be fungicides, insecticides, nematocides, miticides, arthropodicides, bactericides or combinations thereof that are compatible with the compounds of the present invention in the medium selected for application, and not antagonistic to the activity of the present compounds. Accordingly, in such embodiments the other pesticidal compound is employed as a supplemental toxicant for the same or for a different pesticidal use. The compounds and the pesticidal compound in the combination can generally be present in a weight ratio of from 1:100 to 100:1.

The present invention includes within its scope methods for the control or prevention of fungal attack. These methods comprise applying to the locus of the fungus, or to a locus in which the infestation is to be prevented (for example applying to cereal or grape plants), a fungicidal amount of one or more of the compounds. The compounds are suitable for treatment of various plants at fungicidal levels, while exhibiting low phytotoxicity. The compounds are useful in a protectant or eradicant fashion. The compounds are applied by any of a variety of known techniques, either as the compounds or as formulations comprising the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The compounds have been found to have significant fungicidal effect particularly for agricultural use. Many of the compounds are particularly effective for use with agricultural crops and horticultural plants, or with wood, paint, leather or carpet backing.

In particular, the compounds effectively control a variety of undesirable fungi which infect useful plant crops. Activity has been demonstrated for a variety of fungi, including for example the following representative fungi species: Downy Mildew of Grape (*Plasmopara viticola*—PLASVI); Late Blight of Tomato and Potato (*Phytophthora infestans*—PHYTIN); Apple Scab (*Venturia inaequalis*—VENTIN); Brown Rust of Wheat (*Puccinia recondita*—PUCCRT); Stripe Rust of Wheat (*Puccinia striiformis*—PUCCST); Rice Blast (*Pyricularia oryzae*—PYRIOR); Cercospora Leaf Spot of Beet (*Cercospora beticola*—CERCBE); Powdery Mildew of Wheat (*Erysiphe graminis*—ERYSGT); Leaf Blotch of Wheat (*Septoria tritici*—SEPTTR); Sheath Blight of Rice (*Rhizoctonia solani*—RHIZSO); Eyespot of Wheat (*Pseudocercosporella herpotrichoides*—PSDCHE); Brown Rot of Peach (*Monilinia fructicola*—MONIFC); and Glume Blotch of Wheat (*Septoria nodorum*—LEPTNO).

It will be understood by those in the art that the efficacy of the compound for the foregoing fungi establishes the general utility of the compounds as fungicides.

The compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease inhibiting and phytologically acceptable amount. The term "disease inhibiting and phytologically acceptable amount" refers to an amount of a compound which kills or inhibits the plant disease for which control is desired, but is not significantly toxic to the plant. This amount will generally be from about 1 to about 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.1 to 0.45 grams per square meter $g/m^2$).

EXAMPLES

These examples are provided to further illustrate the invention. They are not meant to be construed as limiting the invention.

Commercially available reagents and solvents were used without further purification unless otherwise noted. Melting points were determined on a Thomas Hoover capillary melting point apparatus and are uncorrected. Proton NMR spectra were obtained using a Varian Gemini 300 MHz spectrometer. Chemical shifts are reported in ppm relative to trimethylsilane, and coupling constants are reported in hertz. Mass spectra were obtained using a Hewlett Packard 5890 Series II gas chromatograph-mass spectrometer (GC/MS) with a 12 meter capillary column containing cross-linked methyl silicone gum phase (0.2 mm id×0.33 μm thickness). The GC conditions were 2 min at 50° C. a 20° C./min increase for 13 min, and 2 min at 300° C. for 17 min total time.

Preparations of Materials Used in Making Compounds 2–10 2-Fluoro-3-methyl-5-phenylthiopyridine (Used to Make Compound Two)

To 0.76 g (4 mmol) of 5-bromo-2-fluoro-3-methylpyridine in 25 mL of tetrahydrofuran (THF) at −78°

C. under nitrogen was added 1.6 mL (4 mmol) of 2.5 M n-butyllithium in hexanes. After the addition, 1 g (4 mmol) of S-phenyl benzenethiosulfonate was added all at once and the mixture was allowed to come to room temperature. After 4 h, the mixture was quenched with dilute aqueous sodium bicarbonate solution and extracted with ethylacetate. The organic phase was dried and evaporated under vacuum to give an oil which was chromatographed on silica gel with ethylacetate/hexane (1:5). The product containing fraction was evaporated and chromatographed on a C18 reverse phase preparative column with 70:30 acetonitrile/water as the eluent at 100 mL/min. The product containing band was extracted several times with methylene chloride, and the methylene chloride phase was washed with water, dried, and evaporated under vacuum to give 0.36 g (41%) of an oil that was used as is in coupling reactions similar to the one above. H-NMR—8.06 (s, 1H), 7.60 (d, 1H, 8.8 Hz), 7.28 (m, 5H).

Chloro-2-fluoro-5-phenylthiopyridine (Used to Make Compound Three)

To 0.93 g (4.4 mmol) of 5-bromo-3-chloro-2-fluoropyridine in 25 mL of ether at −78° C. under nitrogen was added 1.85 mL (4.6 mmol) of 2.5 M n-butyllithium in hexanes. After the addition, 1.11 g (4.4 mmol) of S-phenyl benzenethiosulfonate was added all at once and the mixture was allowed to come to room temperature. After 16 h, the mixture was quenched with dilute aqueous sodium bicarbonate solution. The organic phase was dried and evaporated under vacuum to give an oil which was chromatographed on silica gel with ethylacetate/hexane (1:4). The product containing fraction was evaporated and chromatographed on a C18 reverse phase preparative column with 70:30 acetonitrile/water as the eluent at 100 mL/min. The product containing band at 18.6 min was extracted several times with methylene chloride, and the methylene chloride phase was washed with water, dried, and evaporated under vacuum to give 0.29 g (27%) of an oil. GC/MS showed 100% at 8.9 min with a molecular ion of 239, and the oil was used as is in coupling reactions similar to the one above. H-NMR—8.03 (s, 1H), 7.70 (d, 1H, 8.2 Hz), 7.36 (m, 5H).

3-Chloro-2-fluoro-5-(4-methylphenyl)thiopyridine (Used to Make Compound Four)

To 1.15 g (5.5 mmol) of 5-bromo-3-chloro-2-fluoropyridine in 10 mL of ether at −78° C. under nitrogen was added 2.2 mL (5.5 mmol) of 2.5 M n-butyllithium in hexanes. After the addition, 1.39 g (5 mmol) of S-(p-tolyl)-p-tolylthiosulfonate (next preparation) was added all at once and the mixture was allowed to come to room temperature. After 1 h, the mixture was quenched with dilute aqueous sodium bicarbonate solution. The organic phase was dried and evaporated under vacuum to give an oil which was chromatographed on silica gel with ethylacetate/hexane 1:4 as an eluent. The product containing band was evaporated under vacuum to give 0.56 g of an oil was that was used as is in the coupling reaction above. GC/MS showed that the product was only 69% desired at 12.0 min with a molecular ion of 253.

S(p-tolyl)-p-tolylthiosulfonate

To 4.9 g (20 mmol) of bis-p-tolyldisulfide was added 4.5 g (40 mmol) of 30% hydrogen peroxide solution in 20 mL of glacial acetic acid. The mixture was stirred 16 h, and another equivalent of hydrogen peroxide was added with warming to dissolve all the solids. The mixture was cooled to room temperature, and quenched with ice water. The solids were filtered under vacuum and recrystallized from methanol to give 2.2 g (40%) mp=75–7° C. H-NMR—7.46 (d, 2H, 8.1 Hz), 7.22 (m, 4H), 7.13 (d, 2h, 8.0 Hz), 2.42 (s, 3H), 2.38 (s, 3H).

3-Chloro-2-fluoro-5-(4-chlorophenyl)thiopyridine (Used to Make Compound Five)

To 2.09 g (10 mmol) of 5-bromo-3-chloro-2-fluoropyridine in 25 mL of ether at −78° C. under nitrogen was added 4.0 mL (10 mmol) of 2.5 M n-butyllithium in hexanes. After the addition, 1.79 g (10 mmol) of 4-chlorophenylsulfenyl chloride (next preparation) was added all at once and the mixture was allowed to come to room temperature. After 64 h, the mixture was quenched with dilute aqueous sodium bicarbonate solution. The organic phase was dried and evaporated under vacuum to give an oil which was chromatographed on silica gel with ethylacetate/hexane 1:5. The product containing band was evaporated under vacuum to give 1.0 g (33%). GC/MS showed 70% at 12.5 min with a molecular ion of 273/275, and the oil was used as is to make compound five.

4-Chlorophenylsulfenyl chloride

To 7.2 g (50 mmol) of p-chlorothiophenol in 50 mL of methylene chloride was added 0.1 mL of triethylamine and 4.75 mL (60 mmol) of sulfuryl chloride drop wise with magnetic stirring at 0–5° C. under nitrogen. The mixture was allowed to come to room temperature and stirred 2 h. The mixture was evaporated under vacuum, and the residue vacuum distilled bp=80–100° C. at 30 mm. Yield was 2.07 g, but GC/MS showed only 14% at 8.2 min. The liquid was used as is to make 3-chloro-2-fluoro-5-(4-chlorophenyl)thiopyridine.

2-Fluoro-5-phenylthiopyridine (Used to Make Compound Six)

To 1.76 g (10 mmol) of 5-bromo-2-fluoropyridine in 25 mL of ether at −78° C. under nitrogen was added 4.0 mL (10 mmol) of 2.5 M n-butyllithium in hexanes. After the addition, 1.44 g (10 mmol) of phenylsulfenyl chloride was added all at once and the mixture was allowed to come to room temperature. After 1 h, the mixture was quenched with dilute aqueous sodium bicarbonate solution. The organic phase was dried and evaporated under vacuum to give an oil which was distilled under vacuum. Bp=100–10° C. at 0.5 mm. Yield 1.10 g (53%). GC/MS showed 72% at 10.0 min with a molecular ion of 205/207, and the oil was used to make Compound 6.

3-Chloro-2-fluoro-5-(3-methylphenyl)thiopyridine (Used to Make Compound Seven)

To 2.09 g (10 mmol) of 5-bromo-3-chloro-2-fluoropyridine in 25 mL of ether at −78° C. under nitrogen was added 4.0 mL (10 mmol) of 2.5 M n-butyllithium in hexanes. After the addition, 1.59 g (10 mmol) of 3-methylphenylsulfenyl chloride (next preparation) was added all at once and the mixture was allowed to come to room temperature. After 1 h, the mixture was quenched with dilute aqueous sodium bicarbonate solution. The organic phase was dried and evaporated under vacuum to give an oil which was distilled under vacuum. Bp=132–40° C. at 0.015 mm. Yield 1.36 g (54%), and the oil was used as is to make compound seven.

3-Methylphenylsulfenyl chloride

To 6.21 g (50 mmol) of 3-methylthiophenol in 10 mL of methylene chloride was added 0.1 mL of triethylamine and then 4.75 mL (60 mmol) of sulfuryl chloride drop wise under nitrogen. After the addition, the mixture was evaporated under vacuum, and the residue was distilled bp=70° C. at 0.25 mm. Yield 3.3 g (42%), and the liquid was used as is to make 3-chloro-2-fluoro-5-(3-methylphenyl)thiopyridine.

3-Chloro-2-fluoro-5-(3chlorophenyl)thiopyridine (Used to Make Compound Eight)

To 2.09 g (10 mmol) of 5-bromo-3-chloro-2-fluoropyridine in 25 mL of ether at −78° C. under nitrogen was added 4.0 mL (10 mmol) of 2.5 M n-butyllithium in hexanes. After the addition, 1.79 g (10 mmol) of 3-chlorophenylsulfenyl chloride was added all at once and the mixture was allowed to come to room temperature. After 1 h, the mixture was quenched with dilute aqueous sodium bicarbonate solution. The organic phase was dried and evaporated under vacuum to give an oil which was distilled under vacuum. Bp=150–60° C. at 0.5 mm. Yield 1.76 g (64%). GC/MS showed 73% at 11.7 min with a molecular ion of 273/275, and the oil was used as is to make Compound Eight.

Methyl, 2-keto-[2-(3-chloro-5-phenylthio-2-pyridyloxy)methylphenyl]acetate (Used to Make Compound Nine)

To 0.7 g (1.5 mmol) of 2-(3-chloro-5-phenylthio-2-pyridyloxy)methyl-iodobenzene (next preparation) in 10 mL of THF at −78° C. under nitrogen was added 0.6 mL of n-butyllithium in hexanes. To the cold mixture was added a pre-mixed solution of 0.27 g (3 mmol) of lithium bromide and 0.22 g (1.5 mmol) of cuprous bromide in 5 mL of THF. To the cold mixture the copper reagent was added 0.19 g (1.5 mmol) of methyl chlorooxalate, and after 45 min, the reaction mixture was allowed to come to room temperature and partitioned between ether and saturated aqueous ammonium chloride solution. The organic phase was dried, evaporated under vacuum, and chromatographed on silica gel with ethylacetate/hexane 1:5 as the eluent. The product containing band was evaporated under vacuum to give 0.20 g (31%) of the desired keto-ester. H-NMR—8.10 (d, 1H, 2.1 Hz), 7.70 (d, 2H, 7.3 Hz), 7.71 (d, 1H, 2.1 Hz), 7.65 (t, 1H, 6.1 Hz), 7.45 (t, 1H, 6.2 Hz), 7.2–7.34 (m, 5H), 5.83 (s, 2H), 3.95 (s, 3H).

2-(3-Chloro-5-phenylthio-2-pyridyloxy)methyl-iodobenzene

Sodium hydride 60% in mineral oil (0.17 g–4.4 mmol) was washed with hexanes. To the hexane wet solids were added 5 mL of dry THF and 1 mL of dry dimethylsulfoxide (DMSO) under nitrogen. To the mixture was added 1.02 g (4.4 mmol) of 2-hydroxymethyl iodobenzene. After stirring a few minutes at ambient temperature, 1.04 g (4.4 mmol) of 3-chloro-2-fluoro-5-phenylthiopyridine was added, and the mixture was allowed to stir for 16 h. The mixture was partitioned between ether and dilute aqueous sodium bicarbonate solution. The organic phase was dried and evaporated to give 1.9 g (96% crude) of the desired coupling product that was used as is to make methyl, 2-keto-[2-(3-chloro-5-phenylthio-2-pyridyloxy)methylphenyl]acetate. H-NMR—8.14 (d, 1H, 2.1 Hz), 7.86 (d, 1H, 7.9 Hz), 7.72 (d, 1H, 2.1 Hz), 7.54 (d, 1H, 7.9 Hz), 7.38, (t, 1H, 7.1H), 7.2–7.3 (m, 5H), 7.03 (t, 1H, 7.0 Hz), 5.43 (s, 2H). e 25 m column; 50° C. for 2 min then 20° C./min temperature increase to 300° C.

Preparations of Compounds 2–10 2-Methoxyimino-N-methyl-[3-methyl-2-(5-phenylthio-2-pyridyloxy)methylphenyl]acetamide (Compound Two)

To 0.44 g (1.9 mmol) of 2-methoxyimino-N-methyl-(2-hydroxymethyl phenyl)acetamide and 2.0 mL of 1M potassium tert-butoxide in THF was added 0.41 g (1.9 mmol) of 2-fluoro-3-methyl-5-phenylthiopyridine under nitrogen. The mixture was stirred for 2 h at room temperature and quenched with dilute aqueous sodium bicarbonate solution. The product was extracted into diethyl ether (ether), dried over anhydrous sodium sulfate (dried), and evaporated under vacuum to give an oil. The residue was chromatographed on silica gel with ethylacetate/hexane 1:4 the 3:8 as an eluent. The product containing fraction was evaporated under vacuum to give 0.61 g (74%) of a z/e mixture (1:5) as a glass. C13 reverse phase chromatography on an analytical column with acetonitrile/water 70:30) as an eluent at 1 mL/min showed 100% at 13.3 min. H-NMR (e)- 8.05 (d, 1H, 2.7 Hz), 0.58 (d, 1H, 7.7 Hz), 7.35–7.50 (m, 3H), 7.15–7.28 (m, 6H), 6.74 (1H), 5.28 (s, 2H), 3.94 (s, 3H), 2.88 (d, 3H, 4.8 Hz), 2.14 (s, 3H).

2-Methoxyimino-N-methyl-[2-(3-chloro-5-phenylthio-2-pyridyloxy)methylphenyl]acetamide (Compound Three)

To 0.37 g (1.6 mmol) of 2-methoxyimino-N-methyl-(2-hydroxymethyl phenyl)acetamide and 1.7 mL of 1M potassium tert-butoxide in THF was added 0.40 g (1.7 mmol) of 3-chloro-2-fluoro-5-phenylthiopyridine under nitrogen. The mixture was stirred for 16 h at room temperature and quenched with dilute aqueous sodium bicarbonate solution. The product was extracted into diethyl ether (ether), dried over anhydrous sodium sulfate (dried), and evaporated under vacuum to give an oil. The residue was chromatographed on silica gel with ethylacetate/hexane (1:4) then (1:2) as an eluent. The product containing fraction was evaporated under vacuum and crystallized from toluene/hexane (1:1) to give 0.48 g (65%) mp=84–6° C. as an e/z mixture (1:6). H-NMR (e)- 0.04 (d, 1H, 2.1 Hz), 7.66 (d, 1H, 2.1 Hz), 7.60 (d, 1H, 7.6 Hz), 7.4 (m, 2H), 7.21–7.31 (6H), 6.73 (1H), 5.32 (s, 2H), 3.94 (s, 3H), 2.88 (d, 3H, 4.8 Hz).

2-Methoxyimino-N-methyl-{3-chloro-2-[5-(4-methylphenyl)thio-2-pyridyloxy]methylphenyl}acetamide (Compound Four)

To 0.34 g (1.5 mmol) of 2-methoxyimino-N-methyl-(2-hydroxymethyl phenyl)acetamide and 1.5 mL of 1M potassium tert-butoxide in THF was added 0.39 g (1.5 mmol) of 3-chloro-2-fluoro-5-(4-methylphenyl)thiopyridine under nitrogen. The mixture was stirred for 16 h at room temperature and quenched with dilute aqueous sodium bicarbonate solution. The product was extracted into diethyl ether (ether), dried over anhydrous sodium sulfate (dried), and evaporated under vacuum to give an oil. The residue was chromatographed on silica gel with ethylacetate/hexane (1:4) as an eluent. The product containing fraction was evaporated under vacuum to give 0.10 g of the desired coupling product which was crystallized from hexane/toluene to give 80 mg (12%) of a solid mp=100–2° C. H-NMR—7.99 (d, 1H, 2.1 Hz), 7.60 (d, 1H, 2.1 Hz), 7.58 (d, 1H, 7.5 Hz), 7.38 (m, 2H), 7.18–7.24 (m, 3H), 7.20 (d, 1H, 7.5 Hz), 6.75 (1H), 5.31 (s, 2H), 3.93 (s, 3H), 2.87 (d, 3H, 5.1 Hz), 2.31, (s, 3H).

2-Methoxyimino-N-methyl-{3-chloro-2-[5-(4-chlorophenyl)thio-2-pyridyloxy]methylphenyl}acetamide (Compound Five)

To 0.27 g (1.2 mmol) of 2-methoxyimino-N-methyl-(2-hydroxymethyl phenyl)acetamide and 1.2 mL of 1M potassium tert-butoxide in THF was added 0.34 g (1.2 mmol) of 3-chloro-2-fluoro-5-(4-chlorophenyl)thiopyridine under nitrogen. The mixture was stirred for 16 h at room temperature and quenched with dilute aqueous sodium bicarbonate solution. The product was extracted into diethyl ether (ether), dried over anhydrous sodium sulfate (dried), and evaporated under vacuum to give an oil. The residue was crystallized from toluene/hexane. Yield 0.17 g (29%) mp=116–118° C.

2-Methoxyimino-N-methyl-[2-(5-phenylthio-2-pyridyloxy)methyl phenyl]acetamide (Compound Six)

To 0.86 g (3.9 mmol) of 2-methoxyimino-N-methyl-(2-hydroxymethyl phenyl)acetamide and 3.9 mL of 1M potassium tert-butoxide in THF was added 0.79 g (3.9 mmol) of 2-fluoro-5-phenylthiopyridine under nitrogen. The mixture was stirred for 16 h at room temperature and quenched with dilute aqueous sodium bicarbonate solution. The product was extracted into diethyl ether (ether), dried over anhydrous sodium sulfate (dried), and evaporated under vacuum to give an oil. The residue was chromatographed on silica gel with ethylacetate/hexane (1:4) as an eluent. The product containing fraction was evaporated under vacuum and crystallized from toluene/hexane (1:1) to give 0.9 g (57%) mp=95–6° C. LC/MS showed a 407 molecular ion.

2-Methoxyimino-N-methyl-{3-chloro-2-[5-(3-methylphenyl)thio-2-pyridyloxy] methylphenyl}acetamide (Compound Seven)

To 1.04 g (4.7mmol) of 2-methoxyimino-N-methyl-(2-hydroxymethyl phenyl)acetamide and 4.7 mL of 1M potassium tert-butoxide in THF was added 1.28 g (4.7 mmol) of 3-chloro-2-fluoro-5-(3-methylphenyl)thiopyridine under nitrogen. The mixture was stirred for 16 h at room temperature and quenched with dilute aqueous sodium bicarbonate solution. The product was extracted into diethyl ether (ether), dried over anhydrous sodium sulfate (dried), and evaporated under vacuum to give an oil. The residue was chromatographed on silica gel with ethylacetate/hexane (1:4) as an eluent. The product containing fraction was evaporated under vacuum to give 0.57 g (26%) of the desired coupling product as a glass. H-NMR 8.03 (d, 1H, 2.1 Hz), 7.65 (d, 1H, 2.1 Hz), 7.60 (d, 1H, 8.1 Hz), 7.41 (m, 2H), 7.15–7.24 (m, 3H), 7.05 (t, 2H, 8.0 Hz), 6.74 (1H), 5.32 (s, 2H), 3.94 (s, 3H), 2.89 (d, 3H, 5.3 Hz), 2.30 (s, 3H).

2-Methoxyimino-N-methyl-{3-chloro-2-[5-(3-chlorophenyl)thio-2-pyridyloxy] methylphenyl}acetamide (Compound Eight)

To 1.04 g (4.7mmol) of 2-methoxyimino-N-methyl-(2-hydroxymethyl phenyl)acetamide and 4.7 mL of 1M potassium tert-butoxide in THF was added 1.28 g (4.7 mmol) of 3-chloro-2-fluoro-5-(3-chlorophenyl)thiopyridine under nitrogen. The mixture was stirred for 16 h at room temperature and quenched with dilute aqueous sodium bicarbonate solution. The product was extracted into diethyl ether (ether), dried over anhydrous sodium sulfate (dried), and evaporated under vacuum to give an oil. The residue was chromatographed on silica gel with ethylacetate/hexane (1:4) as an eluent. The product containing fraction was evaporated under vacuum to give 0.9 g (40%) of the desired coupling product as a glass. LC/MS showed a molecular ion of 476/8. H-NMR 8.08 (d, 1H, 2.1 Hz), 7.70 (d, 1H, 2.0 Hz), 7.60, (d, 1H, 7.9 Hz), 7.40 (m, 2H), 7.14–7.26 (m, 4H), 7.07 (d, 1H, 7.9 Hz), 6.80 (1H), 5.34 (s, 2H), 3.95 (s, 3H), 2.90 (d, 7.1 Hz).

E-Methyl, 2-methoxyimino-[2-(3-chloro-5-phenylthio-2-pyridyloxy)methyl phenyl]acetate (Compound Nine)

To 0.15 g (0.36 mmol) of methyl, 2-keto-[2-(3-chloro-5-phenylthio-2-pyridyloxy)methylphenyl]acetate in 3 mL of pyridine was added 30 mg (0.36 mmol) of methoxyamine hydrochloride. The mixture was heated to 90° C. on a steam bath for 2 h. The mixture was cooled to room temperature and partitioned between ether and water. The organic phase was dried, evaporated under vacuum, and chromatographed on silica gel with ethylacetate/hexane 1:4 as an eluent. The first product containing band was evaporated under vacuum to give 30 mg (19%) of the desired e-isomer as a glass. HNMR—8.04 (d, 1H, 2.7 Hz), 7.66 (d, 1H, 2.8 Hz), 7.61 (d, 1H, 7.0 Hz), 7.42 (m, 2H), 7.2–7.3 (m, 6H), 5.31 (s, 2H), 4.03 (s, 3H), 3.84 (s, 3H), 2.17.

2-[[(3,5-Dichloro-6-phenylthio-2-pyridinyl)oxy] methyl]-α-methoxyimino)-N-methyl-benzeneacetamide (Compound Ten)

2-[[(3,5,6-trichloro-2-pyridinyl)oxy]methyl]-α-(methoxyimino)-N-methyl-benzeneacetamide (1.0 g, 2.48 mmol) was dissolved with stirring in DMSO (20 mL) and sodium thiophenoxide (0.5 g, 3.79 mmol) added. The reaction mixture was heated at 70° C. for 24 hours, allowed to cool to room temperature and poured into water. It was extracted with ethyl acetate (3×20 mL), and the combined organic extracts washed with water and brine and dried over anhydrous sodium sulphate. Evaporation of the solvent and recrystallization of the residue from ethyl acetate: hexane gave the product as a tan solid (0.89 g, 76%), mp. 149–151° C.

Compounds 11–34 can be made in a manner similar to the procedure used to make Compound 10.

Biological Testing

Compounds 2–34 were formulated at 100 ppm in 10 vol % acetone plus 90 vol % TritonX water (deionized water 99.99 wt % and 0.01 wt % Triton X100). The compounds were then tested for ability to control plant disease on the whole plant in a 1-day protectant test (1DP). Chemicals were sprayed on a turn table sprayer fitted with two opposing air atomization nozzles which delivered approximately 1000 L/ha of spray volume. Plants were inoculated with spores of the fungus the next day, then incubated in an environment conducive to disease development. Disease severity was evaluated 4 to 19 days later, depending on the speed of disease development.

The following experiments were performed in the laboratory to determine the fungicidal efficacy of the compounds of the invention.

Late Blight of Tomatoes (*Phytophthora infestans*—PHYTIN): Tomatoes (cultivar Rutgers) were grown from seed in a soilless peat-based potting mixture (Metromix) until the seedlings were 1–2 leaf (BBCH 12). These plants were then sprayed to run off with the formulated test compound at a rate of 100 ppm. After 24 hours the test plants were inoculated with an aqueous spore suspension of *Phytophthora infestans* and incubated overnight in a dew chamber. The plants were then transferred to the greenhouse until disease developed on the untreated control plants.

Powdery Mildew of Wheat (*Erysiphe graminis*—ERYSGT): Wheat (cultivar Monon) was grown in a soilless peat-based potting mixture (Metromix) until the seedlings were 1–2 leaf (BBCH 12). These plants were then sprayed to run off with the test compound at a rate of 100 ppm. After 24 hours the test plants were transferred to the greenhouse and inoculated with *Erysiphe graminis* by dusting spores from stock plants onto the test plants. The plants were then held in the greenhouse until disease developed on the untreated control plants.

Glume blotch of wheat (*Leptosphaeria nodorum*—LEPTNO): Wheat (cultivar Monon) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Leptosphaeria nodorum* and incubated in a dew chamber overnight. The plants were then transferred to the greenhouse until disease developed on the untreated control plants.

Brown rust (*Puccinia recondita*—PUCCRT): Wheat (cultivar Monon) was grown from seed in a soilless peat-based potting mixture (Metromix) until the seedlings were 1–2 leaf (BBCH 12). These plants were then sprayed to run off with the test compound at a rate of 100 ppm. After 24 hours the test plants were inoculated with an aqueous spore suspension of *Puccinia recondita* and incubated overnight in a dew chamber. The plants were then transferred to the greenhouse until disease developed on the untreated control plants.

The following table presents the activity of typical compounds of the present invention when evaluated in these experiments. The effectiveness of the test compounds in controlling disease was rated by giving the percent control of the plant disease compared with untreated, inoculated plants.

TABLE ONE

Inventive Compounds

| Compound Number | J | Q | L$^2$ | L$^1$ |
|---|---|---|---|---|
| 2 | NH | Ph | Me | H |
| 3 | NH | Ph | Cl | H |
| 4 | NH | 4-MePh | Cl | H |
| 5 | NH | 4-ClPh | Cl | H |
| 6 | NH | Ph | H | H |
| 7 | NH | 3-MePh | Cl | H |
| 8 | NH | 3-ClPh | Cl | H |
| 9 | O | Ph | Cl | H |

Biological Data

| Compound Number | ERYSGT | LEPTNO | PHYTIN | PUCCRT |
|---|---|---|---|---|
| 3 | 85 | 90 | 90 | 98 |
| 4 | 67 | 98 | 89 | 99 |
| 5 | 85 | 98 | 99 | 100 |
| 6 | 80 | 98 | 90 | 98 |
| 7 | 98 | 98 | 100 | 100 |
| 8 | 98 | 98 | 100 | 98 |

TABLE TWO

Compounds

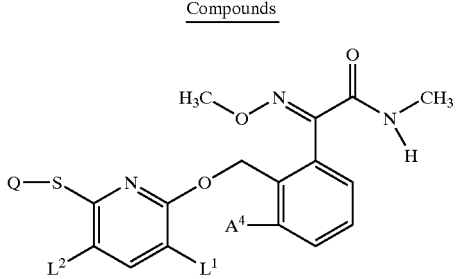

| Compound Number | A$^4$ | Q | L$^1$ | L$^2$ |
|---|---|---|---|---|
| 10 | H | Ph | Cl | Cl |
| 11 | H | 4-ClPh | Cl | Cl |
| 12 | H | Ph | H | CF$_3$ |
| 13 | H | 4-CF$_3$Ph | Cl | Cl |
| 14 | H | Ph | H | H |
| 15 | H | 4-MePh | H | H |
| 16 | H | 3-MePh | H | H |
| 17 | H | 2-MePh | H | H |
| 18 | H | 4-iPrPh | H | H |
| 19 | H | 4-BrPh | H | H |
| 20 | H | 4-ClPh | H | H |
| 21 | H | β-naphthyl | H | H |
| 22 | H | 3-CF$_3$Ph | H | H |
| 23 | H | 3-ClPh | H | H |
| 24 | H | 4-FPh | H | H |
| 25 | H | 2-ClPh | H | H |
| 26 | H | 2,6-(CH$_3$)$_2$Ph | H | H |
| 27 | H | 2-FPh | H | H |
| 28 | H | 4-Cl-2-MePh | H | H |
| 29 | H | 2-CF$_3$Ph | H | H |
| 30 | H | 3-FPh | H | H |
| 31 | H | α-naphthyl | H | H |
| 32 | H | Ph | F | F |
| 33 | H | 2-C$_2$H$_5$Ph | H | H |
| 34 | F | Ph | H | H |

Biological Data

| Compound Number | ERYSGT | LEPTNO | PHYTIN | PUCCRT |
|---|---|---|---|---|
| 10 | 99 | 98 | 96 | 100 |
| 11 | 69 | 0 | 44 | 89 |
| 12 | 98 | 78 | 94 | 100 |
| 13 | 98 | 0 | 0 | 98 |
| 14 | 92 | 89 | 100 | 100 |
| 15 | 92 | 67 | 100 | 100 |
| 16 | 92 | 89 | 100 | 100 |
| 17 | 92 | 98 | 100 | 100 |
| 18 | 98 | 98 | 99 | 100 |
| 19 | 98 | 98 | 100 | 100 |
| 20 | 92 | 98 | 100 | 100 |
| 21 | 92 | 98 | 100 | 100 |
| 22 | 92 | 78 | 100 | 98 |
| 23 | 98 | 78 | 100 | 100 |
| 24 | 85 | 98 | 100 | 100 |
| 25 | 77 | 98 | 94 | 100 |
| 26 | 69 | 89 | 100 | 98 |
| 27 | 77 | 98 | 100 | 100 |
| 28 | 98 | 98 | 100 | 100 |
| 29 | 98 | 78 | 100 | 100 |
| 30 | 98 | 98 | 100 | 100 |
| 31 | 92 | 98 | 100 | 100 |
| 32 | 77 | 98 | 100 | 100 |
| 33 | 92 | 98 | 100 | 100 |
| 34 | 85 | 98 | 94 | 100 |

We claim:

1. A compound having the following formula

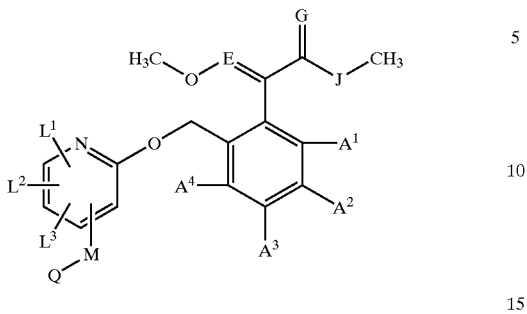

wherein

- $A^1$, $A^2$, $A^3$, and $A^4$ are independently selected from the group consisting of hydro (—H), halo (—F, —Cl, —Br, and —I), and methyl (—CH$_3$);
- E is selected from the group consisting of aza (—N═) and methine (—CH═);
- G is selected from the group consisting of oxo (O═) and thioxo (S═);
- J is selected from the group consisting of oxy (—O—), amino (—NH—) and alkylamino (—NT$^1$—) where T$^1$ is an alkyl group having 1 to 6 carbon atoms;
- $L^1$, $L^2$, and $L^3$ are independently selected from the group consisting of hydro (—H), halo (—F, —Cl, —Br, and —I), cyano (—CN), methyl (—CH$_3$), and mono, di, and trihalomethyl;
- M is selected from the group consisting of thio (—S—), and sulfinyl (—S(═O)—); and
- Q is selected from the group consisting of phenyl and substituted phenyl where said substituted phenyl has one or more substituents that are independently selected from the group consisting $C_1$-$C_6$ alkyl, halo-$C_1$-$C_6$ alkyl, halo, nitro, cyano, arylalkyl, amino, and substituted amino.

2. A compound according to claim 1 wherein said $A^1$, $A^2$, $A^3$, and $A^4$ are independently selected from the group consisting of hydro (—H), and halo (—F, —Cl, —Br, and —I).

3. A compound according to claim 2 wherein said E is aza (—N═).

4. A compound according to claim 3 wherein said G is oxo (O═).

5. A compound according to claim 4 wherein said J is selected from the group consisting of oxy (—O—), and amino (—NH—).

6. A compound according to claim 5 wherein said $L^1$, $L^2$, and $L^3$ are independently selected from the group consisting of hydro (—H), halo (—F, —Cl, —Br, and —I), methyl (—CH$_3$), and mono, di, and trihalomethyl.

7. A compound according to claim 6 wherein said M is thio (—S—).

8. A compound according to claim 7 wherein said Q is an unsubstituted phenyl.

9. A process comprising reacting a compound of formula two with a compound of formula three

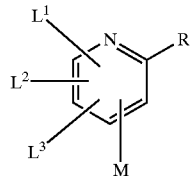

Formula Two

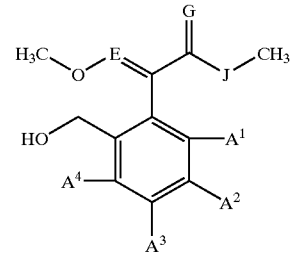

Formula Three to produce a compound according to claim 1, wherein

- R is selected from the group consisting of halo (—F, —Cl, —Br, and —I) and alkylsulfonyl (—S(═O)$_2$—T$^2$ where T$^2$ is an alkyl group having from 1 to 6 carbon atoms.
- $A^1$, $A^2$, $A^3$, and $A^4$ are independently selected from the group consisting of hydro (—H), halo (—F, —Cl, —Br, and —I), and methyl (—CH$_3$);
- E is selected from the group consisting of aza (—N═) and methine (—CH═);
- G is selected from the group consisting of oxo (O═) and thioxo (S═);
- J is selected from the group consisting of oxy (—O—), amino (—NH—) and alkylamino (—NT$^1$—) where T$^1$ is an alkyl group having 1 to 6 carbon atoms;
- $L^1$, $L^2$, and $L^3$ are independently selected from the group consisting of hydro (—H), halo (—F, —Cl, —Br, and —I), cyano (—CN), methyl (—CH$_3$), and mono, di, and trihalomethyl;
- M is selected from the group consisting of thio (—S—), and sulfinyl (—S(═O)—); and
- Q is selected from the group consisting of unsubstituted phenyl and substituted phenyl where said substituted phenyl has one or more substituents that are independently selected from the group consisting $C_1$-$C_6$ alkyl, halo-$C_1$-$C_6$ alkyl, halo, nitro, cyano, arylalkyl, amino, and substituted amino.

10. A process according to claim 9 wherein said $A^1$, $A^2$, $A^3$, and $A^4$ are independently selected from the group consisting of hydro (—H), and halo (—F, —Cl, —Br, and —I).

11. A process according to claim 10 wherein said E is aza (—N═).

12. A process according to claim 11 wherein said G is oxo (O═).

13. A process according to claim 12 wherein said J is selected from the group consisting of oxy (—O—), and amino (—NH—).

14. A process according to claim 13 wherein said $L^1$, $L^2$, and $L^3$ are independently selected from the group consisting of hydro (—H), halo (—F, —Cl, —Br, and —I), methyl (—CH$_3$), and mono, di, and trihalomethyl.

15. A process according to claim 14 wherein said M is thio (—S—).

16. A process according to claim 15 wherein said Q is an unsubstituted phenyl.

17. A process of applying a compound according to claim 1, in a fungicidal amount, to a locus to control fungi.

18. A process of applying a compound according to claim 2, in a fungicidal amount, to a locus to control fungi.

19. A process of applying a compound according to claim 3, in a fungicidal amount, to a locus to control fungi.

20. A process of applying a compound according to claim 4, in a fungicidal amount, to a locus to control fungi.

21. A process of applying a compound according to claim 5, in a fungicidal amount, to a locus to control fungi.

22. A process of applying a compound according to claim 6, in a fungicidal amount, to a locus to control fungi.

23. A process of applying a compound according to claim 7, in a fungicidal amount to a locus to control fungi.

24. A process of applying a compound according to claim 8, in a fungicidal amount to a locus to control fungi.

\* \* \* \* \*